US012661164B2

(12) United States Patent
    Knöpfle

(10) Patent No.: US 12,661,164 B2
(45) Date of Patent: Jun. 23, 2026

(54) BONE FIXATION DEVICE

(71) Applicant: iAccess MedTec GmbH, Freiburg (DE)

(72) Inventor: Christian Knöpfle, Bremgarten (DE)

(73) Assignee: iAccess MedTec GmbH, Freiburg (DE)

( * ) Notice: Subject to any disclaimer, the term of this patent is extended or adjusted under 35 U.S.C. 154(b) by 164 days.

(21) Appl. No.: 18/708,053

(22) PCT Filed: Feb. 27, 2023

(86) PCT No.: PCT/EP2023/054824
    § 371 (c)(1),
    (2) Date: May 7, 2024

(87) PCT Pub. No.: WO2023/165926
    PCT Pub. Date: Sep. 7, 2023

(65) Prior Publication Data
    US 2026/0047875 A1      Feb. 19, 2026

(30) Foreign Application Priority Data
    Mar. 2, 2022    (EP) .................................... 22159703

(51) Int. Cl.
    *A61B 17/82*      (2006.01)
    *B33Y 80/00*      (2015.01)
(52) U.S. Cl.
    CPC ............ *A61B 17/823* (2013.01); *B33Y 80/00* (2014.12)
(58) Field of Classification Search
    CPC ............................. A61B 17/82; A61B 17/823
    See application file for complete search history.

(56) References Cited

U.S. PATENT DOCUMENTS

| | | | |
|---|---|---|---|
| 5,993,452 A | 11/1999 | Vandewalle | |
| 10,716,608 B2 * | 7/2020 | Beyersdorf | ........ A61B 17/8861 |
| 2011/0054547 A1 | 3/2011 | Anderson | |
| 2020/0297402 A1 | 9/2020 | Beyersdorf et al. | |
| 2021/0307799 A1 | 10/2021 | Del Medico | |

OTHER PUBLICATIONS

Extended European Search Report EP22159703.2, dated Aug. 25, 2022, 8pp.
International Search Report PCT/EP2023/054824, dated Apr. 19, 2023, 2pp.

* cited by examiner

*Primary Examiner* — Si Ming Ku
(74) *Attorney, Agent, or Firm* — Carter, DeLuca & Farrell LLP

(57) ABSTRACT

A bone fixation device (1) is presented, comprising a wire (7) and a load distributor (9), the load distributor comprising: a contact side (2) having a contact region (11) which is pressed against the bone to be fixed upon tightening of the wire (7), and two opposite lateral sides (4) that are not in contact with the bone upon tightening of the wire (7). At least one of the lateral sides (4) is provided with a plurality of recesses (5) which do not extend into the contact sides (2). The contact side (2) of the load distributor (9) has a continuous smooth surface which is configured to slide across the bone without damaging the bone when the load distributor (9) is pulled longitudinally across the bone during application.

13 Claims, 8 Drawing Sheets

BONE FIXATION DEVICE

TECHNICAL FIELD

The present invention generally relates to surgical devices and in particular to a bone fixation device and a load distributor for a bone fixation device.

BACKGROUND

A fragmented or cut bone often requires application of a bone fixation device which exerts an external force on bone parts by tightly pressing them together. To this end, flexible straps or wires are used which are looped around the bone parts and tightened thereafter similar to a cable tie.

In heart surgery the sternum bone often has to be cut longitudinally in order to obtain access to the heart. After the surgical operation has been completed, the two sternum bone halves have to be joined together again. This is usually done by means of a simple wire or by using a more sophisticated sternum closure device comprising a wire and a load distributor as disclosed in EP 3378424 A1. During application, the known devices are threaded underneath and looped around the bone. Finally, the free ends of the wire are twisted in order to tighten the device and to exert an external force pressing the bone parts together.

The sternum closure device disclosed in EP 3378424 A1 provides a load distributor which is moulded around the wire in order to avoid cutting the bone when the wire is tightened around the bone. The load distributor, however, consists of a plurality of segments that are separated from each other by indentations. Due to the spaced-apart relationship of the individual segments and the segments having edges at their bone contact side, the load distributor may harm the periosteum when the load distributor is pulled longitudinally across the bone surface during application. US 2020/297 402 A1 discloses a bone fixation device (2) comprising a wire (12) and a load distributor surrounding the wire, comprising: a channel extending therethrough in a longitudinal direction; one contact side having a contact region configured to be pressed against the bone to be fixed upon tightening of the wire, and two opposite lateral sides that are not in contact with the bone upon tightening of the wire, wherein the lateral sides are provided with a plurality of recesses. US 2021/307 799 A1 teaches a bone fixation device comprising a load distributor surrounding a wire and having a smooth contact surface. Other bone fixation devices comprising a load distributor are disclosed in US 2011/054 547 A1 and U.S. Pat. No. 5,993,452 A.

SUMMARY

A problem of the present invention does may be seen in providing a bone fixation device that causes less harm to the bone and in particular to the periosteum on application.

According to one aspect of the present invention, a load distributor and a bone fixation device comprising a wire and a load distributor are presented. The load distributor comprises one or two contact sides having a contact region which is pressed against the bone to be fixed upon tightening of the wire. The bone fixation device further comprises two opposite lateral sides that are not in contact with the bone upon tightening of the wire.

According to an embodiment of the invention, one or both contact regions have a smooth contact surface which is configured to slide across the bone without damaging the bone when the load distributor is pulled longitudinally across the bone during application. In some embodiments, there may be one or more injection points in the contact sides resulting from injection moulding of the load distributor. However, these injection points do not extend over the entire width of the load distributor and have a soft contour and therefore do not cause any trauma to the periosteum.

When viewed from the top or from the bottom, the load distributor is preferably formed as a strip-shaped member whose side edges preferably are parallel straight lines. In an embodiment, the load distributor has a constant width at least at a central portion thereof, in particular at the contact region.

For use as a sternum closure, the contact region, i.e., the part of the load distributor which rests on the bone after the device has been applied to the bone, can have a length of 50 mm-70 mm, or may be shorter or longer, depending on the size of the bone to be fixed. The entire length of the load distributor may be 60 mm-80 mm for instance.

At least one of the lateral sides of the load distributor may be provided with one or a plurality of recesses which weaken the material of the load distributor for greater flexibility and to allow for easy separation of excess material of the load distributor protruding beyond the contact region. Thus, a surgeon may shorten the length of the load distributor as required by simply cutting or twisting off the protruding ends. In a preferred embodiment, the recess(es) are exclusively arranged in one or both lateral sides of the load distributor without touching or extending into the contact side, respectively.

If the material of the load distributor is sufficiently soft and flexible, embodiments without lateral recesses are also possible.

In the context of this disclosure, the term "wire" refers to any elongated element, such as. B. a thread, a strap, a ribbon or the like and should not be understood as limited to metal wires.

In some embodiments, the load distributor comprises an anchoring portion for securely fixing the wire, particularly by friction, so that the wire cannot be removed under regular operational conditions. According to an embodiment of the invention, the wire has one or more curved sections in the region of the load distributor which create enough friction so as to securely fix the wire inside the load distributor. The curved section(s) may be provided by pressing or bending the wire. The preformed wire may then be overmoulded by the load distributor.

According to a special embodiment, the wire has an undulated course within the load distributor. In this context, the term "undulated course" relates to any wave-like or zig-zag-course. When the wire creates enough friction within the load distributor, additional gluing is not necessary. In other embodiments, the wire may be glued to the load distributor.

In a preferred embodiment of the load distributor, the contact side has no recesses or indentations within its contact region which could harm the periosteum during application of the device.

In some embodiments, the continuous smooth surface of the contact side extends essentially along the entire length of the load distributor, from a front end of the load distributor to its rear end.

In some embodiments, the load distributor has a slit extending across its entire length which allows assembling the wire after the load distributor has been manufactured. In an embodiment which is also referred to here as "top loader", the slit is provided in a top side of the load distributor, i.e. opposite the contact side. In an embodiment which is also referred to here as "side loader", the slit is provided in one of the lateral sides of the load distributor. The width of the slit may be designed to be a little bit smaller than the diameter of the wire so that the wire has to be pressed through the slit into the interior channel. Once inserted, the wire is retained in the channel, the smaller width of the gap preventing the wire to come out easily.

The aforementioned recess provided in at least one of the lateral sides of the load distributor may be configured as a through hole or as a blind hole, or generally as a hole or bore.

The recess may be located outside the contact region in the area of the free ends of the load distributor. One or more recesses may also be located within the contact region in order to increase flexibility of the load distributor.

In a special embodiment of the load distributor, at least one of the lateral sides is provided with a plurality of recesses. Some of the recesses may be located inside and others outside of the contact region.

As regards manufacturing of the bone fixation device, the load distributor may be moulded around the wire in a moulding process such as injection moulding.

Alternatively, the load distributor may be manufactured by the 3D-printing or any other well-known technology. The load distributor may be made from a mouldable material such as a polymeric material.

In some embodiments, the load distributor may be integrally formed as one single piece. In other embodiments, the load distributor may comprise several parts which are joined after the wire has been inserted into the channel. The various parts of the load distributor may be joined by ultrasonic welding or gluing or other well-known techniques, for instance.

In some embodiments the load distributor is configured axisymmetric about a central longitudinal axis.

The load distributor may be equipped with two contact sides located on two opposite sides thereof. The contact sides can essentially be identical. This allows a surgeon to use the bone fixation device in both directions (regular or top-down) thus making the device easier to use as he/she does not have to pay attention to the orientation of the device.

The free ends of the load distributor may be tapered, making it easier to loop the load distributor around the bone and further causing less trauma to the bone.

In an embodiment, the tapered ends may have one or more edges serving as blades that allow for easier insertion of the device. The edges can substantially extend in a longitudinal direction. They may be curved and/or slanted relatively to a longitudinal direction.

According to an embodiment of the invention, one or both of the contact sides can have a convex in shape.

BRIEF DESCRIPTION ON DRAWINGS

Further details, advantages and aspects of the present invention will become apparent from the following embodiments taken in conjunction with the drawings, wherein:

FIG. 6a is a side view of a wire and hook for use in a load distributor;

FIG. 6b is a top view of the wire and hook assembly of FIG. 6a;

Figures 7A, 7B, 7C:
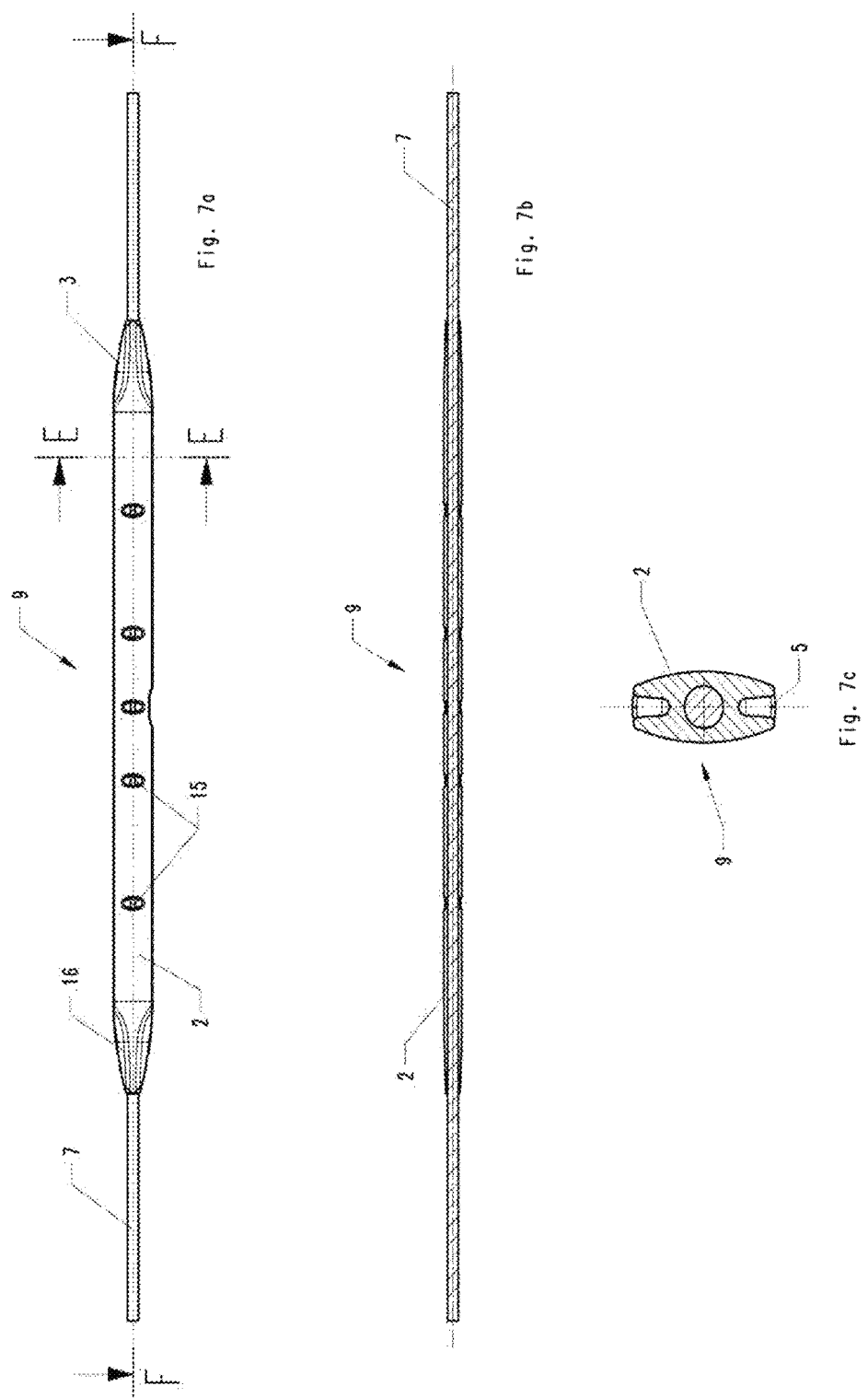

FIGS. 7a-7c various views of an embodiment of a bone fixation device having a cutting tool at its ends.

DETAILED DESCRIPTION

In the following, the same reference numerals will be used to denote the same or similar structural features.

FIGS. 1a-1e show various views of a bone fixation device 1 according to a first embodiment which may be used as a sternum closure in heart surgery for instance. However, the device 1 can also be used for any other indication where parts of a bone have to be fixed by an external force.

The bone fixation device 1 shown in FIGS. 1a-1e essentially comprises a wire 7 and a load distributor 9 which is arranged around the wire 7. During application, the wire 7 is threaded underneath the bone by means of a curved needle 8. Then the surgeon pulls the wire 7 until the load distributor 9 is in the correct position and brings the free ends of the wire 7 together at the proximal side of the bone. Finally, the bone fixation device 1 is tightened simply by twisting the free ends thereby exerting an external force to the bone segments which firmly presses the bone segments together. The load distributor 9 prevents cutting of the wire 7 into the bone as the force exerted by the wire 7 is distributed over a larger area.

In the embodiment of FIGS. 1a-1e, the wire 7 is a metal wire and the load distributor 9 is made of plastics. The load distributor 9 comprises a channel 10 extending therethrough in a longitudinal direction L. The load distributor 9 further has two contact sides 2—one on top and one at the bottom thereof—one of which is pressed against the bone surface upon tightening of the wire 7. The region of the contact side 2 which is in contact with the bone after tightening of the device 1 is referred to as "contact region" 11 (see FIG. 1a). As may be easily understood, the length of the contact region 11 varies depending on the size of the bone. In order to shorten the length of the load distributor 9 as required, the excess material of the load distributor 9 which protrudes beyond the contact region 11 may simply be cut off or twisted off. To this end, the lateral sides 4 of the load distributor 9 each are provided with a plurality of recesses 5 in the form of holes or bores which weaken the material and make it easier to cut off or twist off the ends of the load distributor 9.

Figures 1A, 1B:
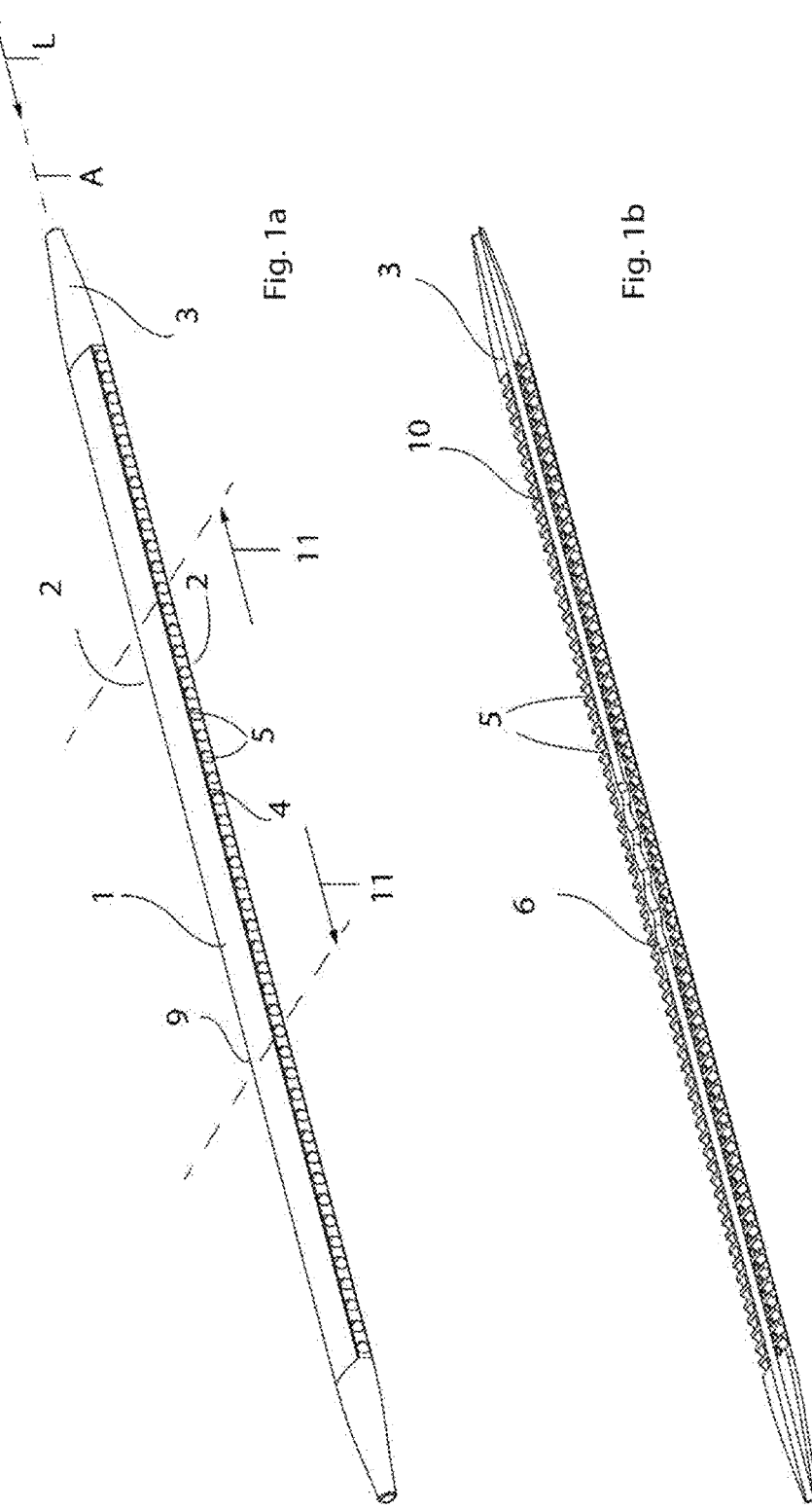
FIG. 1a is a perspective top view of a load distributor of a bone fixation device according to a first embodiment.
FIG. 1b shows a cross-section of the load distributor of FIG. 1a along a central horizontal plane.
Figures 1C, 1D, 1E:
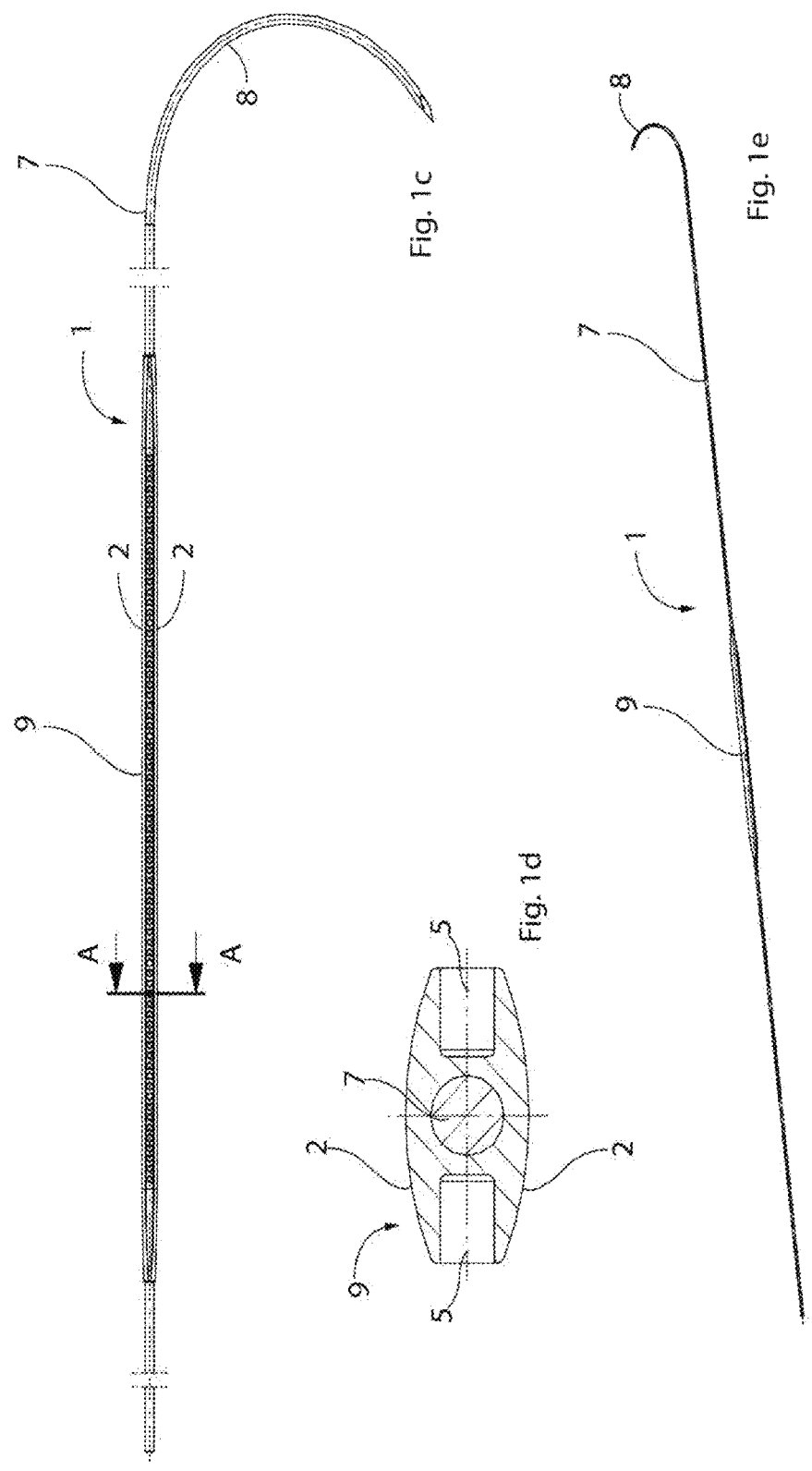
FIG. 1c shows a cross-section of the load distributor of FIG. 1a along a central vertical plane.
FIG. 1d is a cross-sectional view of the load distributor at line A-A shown in FIG. 1c.
FIG. 1e is a perspective view of the bone fixation device according to the first embodiment.

As shown in FIG. 1*a*, the contact sides 2 each have a continuous smooth surface which prevents the bone and in particular the periosteum from getting damaged when the load distributor 9 is pulled longitudinally across the bone during application. FIG. 1*a* also shows that the contact sides 2 have no recesses or indention within the contact region 11 (apart from possible injection points caused by injection moulding). In addition, the load distributor 9 has tapered ends 3 which further contribute to a bone-friendly application.

The load distributor 9 of the first embodiment is configured axisymmetric about a central longitudinal access A.

FIG. 1*b* is a cross-section along a horizontal central plane showing the inner structure of the load distributor 9. As can be seen, the load distributor 9 is provided with an anchoring portion 6 for securely fixing the wire 7. To this end, the wire 7 has one or more curved sections which create enough friction so as to securely fix the wire inside the load distributor 9. The undulated portion of the wire 7 may be wave-like or zig-zag-like for instance, as illustrated.

In the embodiment of FIGS. 1*a*-1*e*, the load distributor is integrally moulded around the wire 7 in an injection moulding process.

Figures 2A, 2B, 2C:
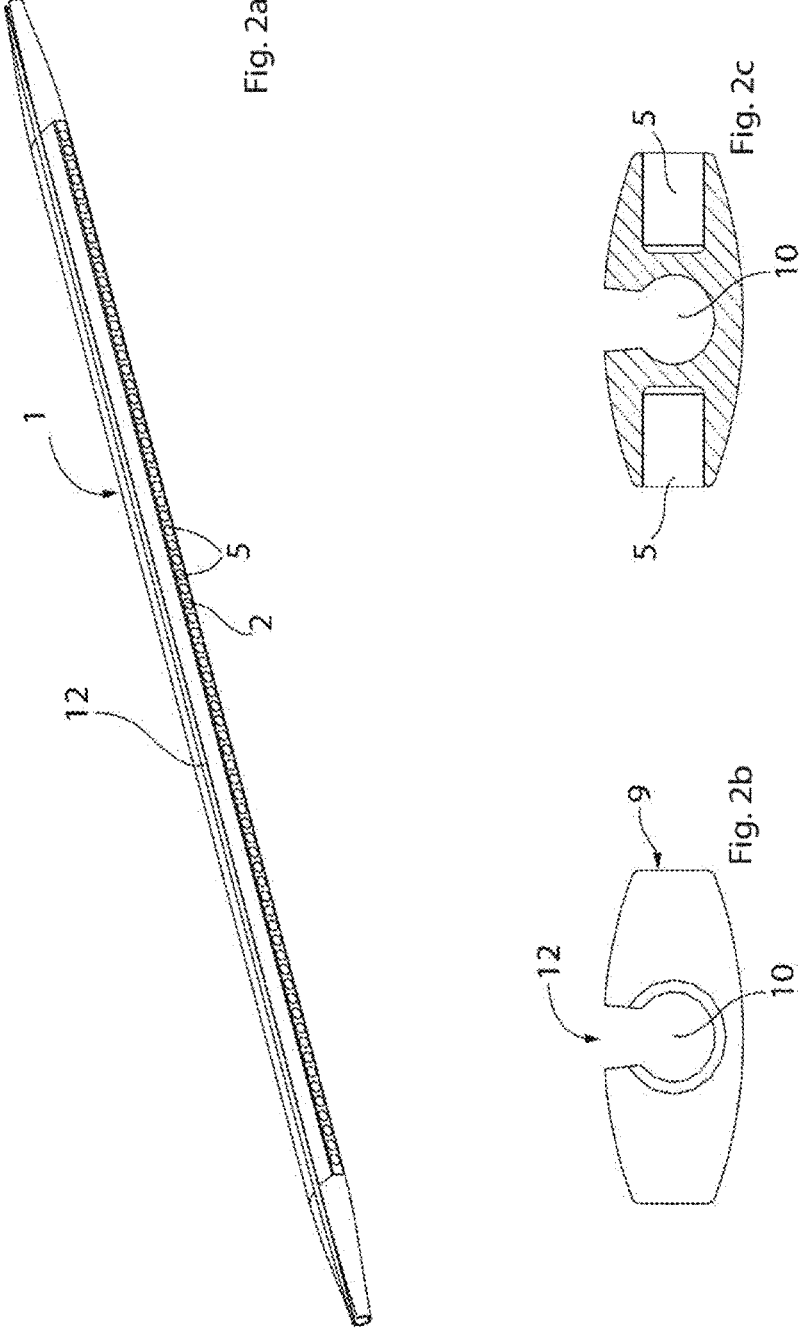
FIG. 2a is a perspective top view of a load distributor of a bone fixation device according to a second embodiment.
FIG. 2b shows the load distributor according to the second embodiment when viewed from a longitudinal direction.
FIG. 2c is a cross-sectional view of the load distributor of the second embodiment.

FIGS. 2*a*-2*c* show various views of a load distributor 9 according to a second embodiment which is also referred to as "top-loader". In this embodiment, the load distributor 9 is manufactured in a first step, for instance by injection moulding, and the wire 7 is assembled via a top side of the load distributor 9 afterwards. To this end, the load distributor 9 comprises a slit 12 extending along its entire length and communicating with the interior channel 10. The width of the slit 12 is smaller than the diameter of the wire 7 so that the wire 7 has to be pressed from the outside into the channel 10. Due to the smaller width of the slit 12, the wire 7 is retained in the channel 10 after assembly.

FIG. 2*b* shows the load distributor 9 according to the second embodiment when viewed from a longitudinal direction L. FIG. 2*c* is a cross-sectional view of the load distributor 9. As can be seen in FIG. 2*c*, the recesses 5 are provided on both lateral sides 4 of the load distributor 9 in the form of blind holes.

Figures 3A, 3B, 3C:
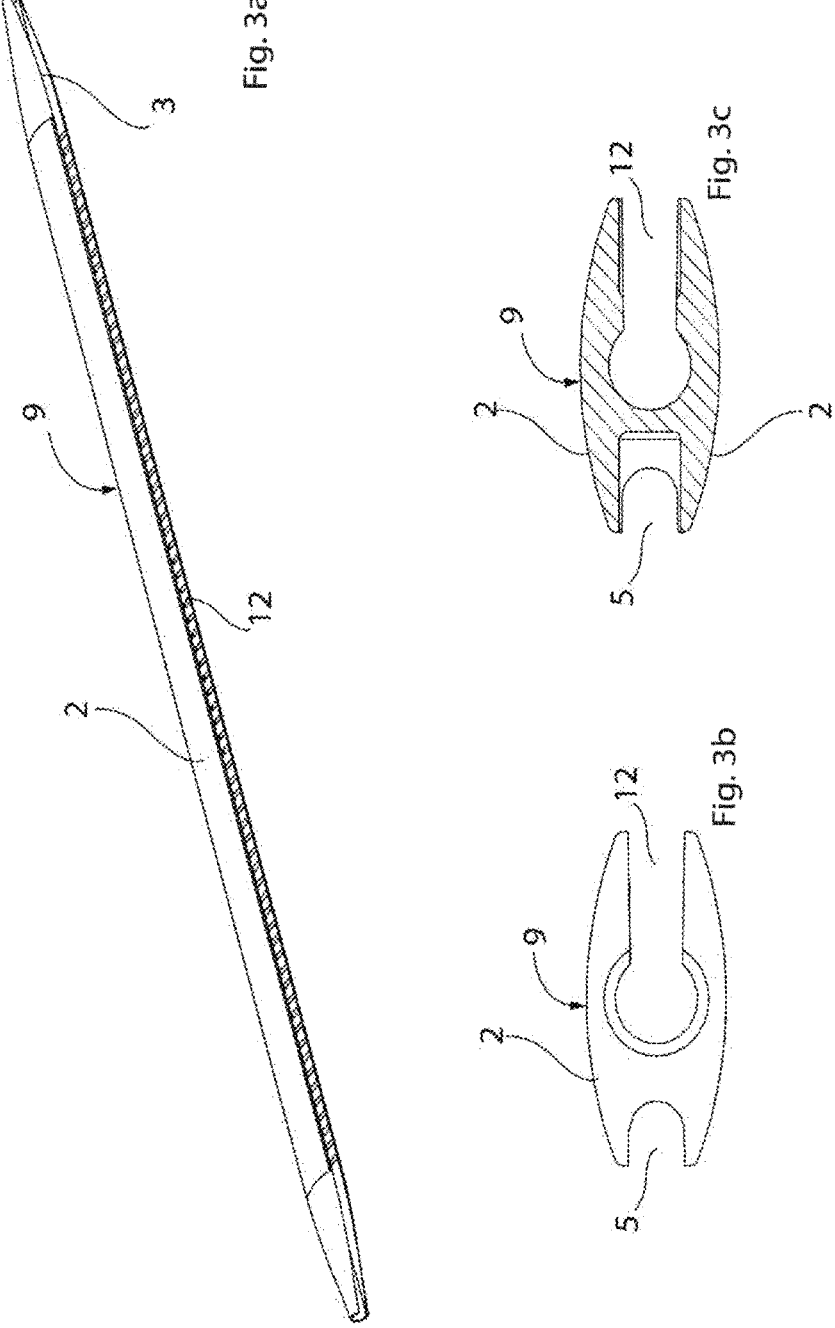
FIG. 3a is a top perspective view of a load distributor according to a third embodiment of the present invention which is also referred to as "side loader"
FIG. 3b shows the load distributor according to the third embodiment when viewed from a longitudinal direction.
FIG. 3c is a cross-sectional view of the load distributor according to the third embodiment.

FIGS. 3*a*-3*c* show various views of a load distributor 9 according to a third embodiment which is also referred to as "side loader". The load distributor 9 comprises a slit 12 extending across the entire length of the load distributor 9, wherein the slit 12 is provided at one lateral side 4 of the load distributor 9. The other lateral side 4 is provided with a number of recesses 5.

FIG. 3*b* shows the load distributor 9 according to the third embodiment when viewed from a longitudinal direction L and FIG. 3*c* is a cross-sectional view of the load distributor 9.

Figures 4A, 4B, 4C:
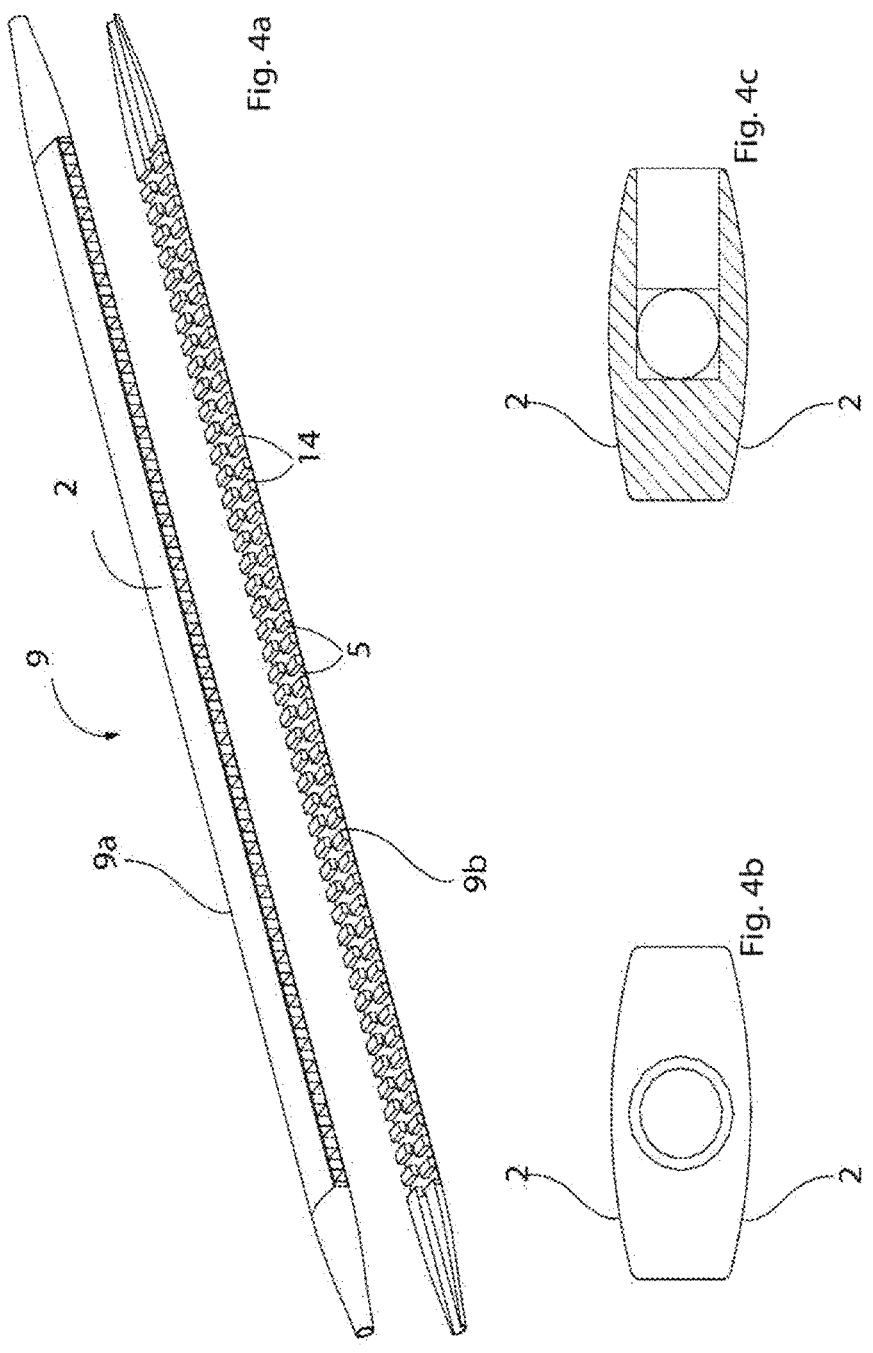
FIG. 4a is a top perspective view of a load distributor according to a fourth embodiment of the present invention comprising two halves.
FIG. 4b shows the load distributor according to the fourth embodiment when viewed from a longitudinal direction.
FIG. 4c is a cross-sectional view of the load distributor according to the fourth embodiment.

FIGS. 4*a*-4*c* show various views of a load distributor 9 according to a fourth embodiment. In this embodiment, each lateral side 4 is provided with a plurality of through holes communicating with the interior channel 10. The holes are arranged side-by-side thereby leaving ribs 14 in between. The ribs 14 arranged on one lateral side 4 of the channel 10 are offset from those located on the other side of the channel 10. Thereby, sort of a stitch pattern is created as shown in FIG. 4*a*.

In the fourth embodiment of FIGS. 4*a*-4*c* the load distributor 9 is made of two halves 9*a*, 9*b* that are manufactured separately and connected to each other after the wire 7 has been inserted into the channel 10. As illustrated, the channel 10 has a curved or undulated section in order to securely fix the wire 7 to the load distributor 9 by friction. FIG. 4*b* shows the load distributor 9 when viewed from the longitudinal direction L with the two halves 9*a*, 9*b* combined. FIG. 4*c* is a cross-sectional view of the load distributor 9 according to the fourth embodiment.

Figure 5:
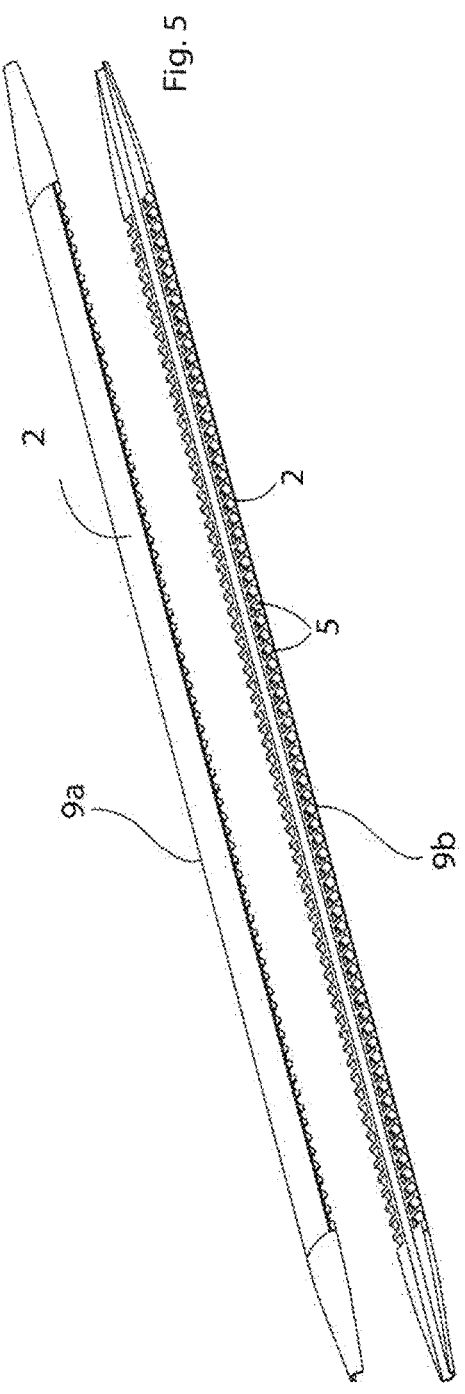
FIG. 5 is a top view of a load distributor according to a fifth embodiment showing two halves of the load distributor before assembly of the wire.

The load distributor 9 shown in FIG. 5 is a made-up of two halves 9*a*, 9*b* which are connected to each other by ultrasonic welding after the wire 7 has been inserted into the channel 10. The load distributor 9 has contact surfaces 2 to at the top and bottom side thereof. The lateral sides 4 are provided with a plurality of recesses 5. The ends 3 of the load distributor 9 are tapered.

Figures 6A, 6B:
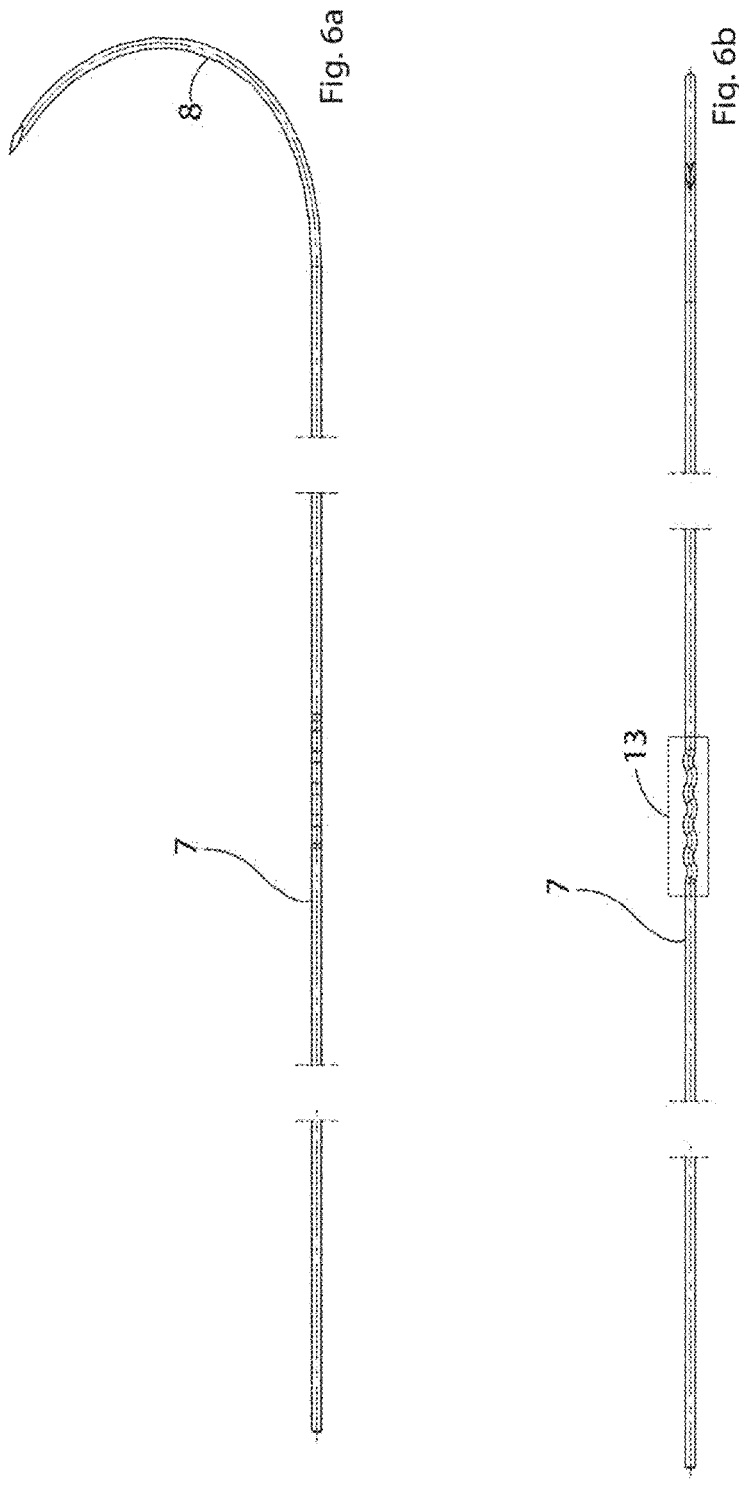

FIG. 6*a* shows a wire 7 and needle 8 assembly in a side view. FIG. 6*b* is a top view of the assembly of FIG. 6*a*. As can be seen in FIG. 6*b*, the wire 7 has an undulated portion 13 which is made by bending or pressing the wire 7 at this region. The undulated portion of the wire 7 engages the anchoring portion 6 of the load distributor 9 thereby preventing the wire 7 from being detached.

FIGS. 7*a*-7*c* show an embodiment of a bone fixation device 1 that has a cutting tool at its ends 3 which allows for easier insertion and pushing of the device. In this embodiment, the cutting tool comprises edges 16 or blades, respectively, formed at the tapered ends 3 of the load distributor. The edges 16 are slightly curved but substantially extend in a longitudinal direction of the device 1.

The load distributor 9 as illustrated in FIG. 7*a* shows several injection points 15 in the contact side 2 resulting from injection moulding. However, these injection points 15 are only due to technical reasons. They do not harm the bone when the device 1 is pulled under the bone.

The invention claimed is:

1. A bone fixation device, comprising:

a wire; and a load distributor surrounding the wire, including:

a channel defined therein and extending therethrough in a longitudinal direction, the channel configured to house the wire therein;

two contact sides located on opposite sides of the load distributor, each of the sides having a contact region configured to be pressed against bone and fixed to bone upon tightening of the wire; and two opposite lateral sides that each remaining spaced from bone upon tightening of the wire, wherein at least one of the lateral sides is provided with one or more holes which do not extend into either of the two contact sides, wherein the two contact sides, at least at their respective contact regions, each have a continuous surface, without any recess or indentation, configured to facilitate sliding the load distributor longitudinally across bone with minimal or no damage to bone.

2. The bone fixation device according to claim 1, wherein the contact sides do not include the one or more recesses at least within the contact region and wherein the contact sides do not define indentations at least within the contact region.

3. The bone fixation device according to claim 1, wherein the continuous surface of the two contact sides extends over substantially an entire length of the load distributor.

4. The bone fixation device according to claim 1, wherein the wire has one or more curved sections which facilitate securing the wire to the load distributor by friction.

5. The bone fixation device according to claim 1, wherein the load distributor has a slit defined therein extending along an entire length thereof, the slit facilitating assembly of the wire after the load distributor has been manufactured.

6. The bone fixation device according to claim 1, wherein the one or more recesses provided in at least one of the lateral sides is configured as a through hole or a blind hole.

7. The bone fixation device according to claim 1, wherein the one or more recesses is located outside the contact region.

8. The bone fixation device according to claim 1, wherein both lateral sides are provided with a plurality of recesses.

9. The bone fixation device according to claim 1, wherein the load distributor is molded around the wire or manufactured by 3D-printing.

10. The bone fixation device according to claim 1, wherein the load distributor includes one or more parts which are connected to each other after the wire has been inserted into the channel.

11. The bone fixation device according to claim 1, wherein the load distributor is axisymmetric about a central longitudinal axis.

12. The bone fixation device according to claim 1, wherein the load distributor has one or two tapered ends.

13. A load distributor for a bone fixation device, comprising:

a channel defined therein and extending therethrough in a longitudinal direction, the channel configured to house a wire therein;

two contact sides located on opposite sides of the load distributor, each of the contact sides having a contact region, wherein at least one of the contact regions is configured to affix against bone upon tightening of the wire; and two opposite lateral sides each remaining spaced from bone upon tightening of the wire, wherein at least one of the two lateral sides is provided with a plurality of holes which do not extend into either of the two contact sides, and wherein the two contact sides, at least at their respective contact regions, each have a continuous surface, without any recess or indentation, configured to facilitate sliding the load distributor longitudinally across bone with minimal or no damage to bone.

* * * * *